United States Patent
Brisander et al.

(10) Patent No.: US 10,933,014 B2
(45) Date of Patent: Mar. 2, 2021

(54) INJECTABLE SUSPENSION COMPRISING 3-BETA-HYDROXY-5-ALPHA-PREGNAN-20-ONE, AND A METHOD FOR THE MANUFACTURING THEREOF

(71) Applicant: ASARINA PHARMA AB, Solna (SE)

(72) Inventors: Magnus Brisander, Ekerö (SE); Karol Horvath, Karlskoga (SE); Björn Norrlind, Stockholm (SE)

(73) Assignee: ASARINA PHARMA AB, Solna (SE)

( * ) Notice: Subject to any disclaimer, the term of this patent is extended or adjusted under 35 U.S.C. 154(b) by 0 days.

(21) Appl. No.: 16/476,377

(22) PCT Filed: Jan. 9, 2018

(86) PCT No.: PCT/EP2018/050453
§ 371 (c)(1),
(2) Date: Jul. 8, 2019

(87) PCT Pub. No.: WO2018/127601
PCT Pub. Date: Jul. 12, 2018

(65) Prior Publication Data
US 2019/0350838 A1     Nov. 21, 2019

(30) Foreign Application Priority Data
Jan. 9, 2017   (SE) .................................. 1750008-3

(51) Int. Cl.
| | |
|---|---|
| A61K 9/00 | (2006.01) |
| A61K 9/10 | (2006.01) |
| A61K 9/16 | (2006.01) |
| A61K 31/57 | (2006.01) |
| A61K 47/14 | (2017.01) |

(Continued)

(52) U.S. Cl.
CPC .......... *A61K 9/0019* (2013.01); *A61K 9/0029* (2013.01); *A61K 9/10* (2013.01);
(Continued)

(58) Field of Classification Search
CPC ...... A61K 9/0019; A61K 9/0029; A61K 9/10; A61K 9/1688; A61K 31/57; A61K 47/14;
(Continued)

(56) References Cited

U.S. PATENT DOCUMENTS 5,939,545 A     8/1999   Upasani et al.

FOREIGN PATENT DOCUMENTS

| WO | WO99/45931 A1 | 9/1999 |
| WO | WO2009/108804 A1 | 9/2009 |

(Continued)

OTHER PUBLICATIONS

Grant, K. A., et al., "Neuroactive steroid stereospecifity of ethanol-like discriminative stimulus effects in monkeys," J. Pharmacol. Exp. Ther. 2008;326(1):354-361.

(Continued)

*Primary Examiner* — Carlos A Azpuru
(74) *Attorney, Agent, or Firm* — Cermak Nakajima & McGowan LLP; Malcolm K. McGowan (57) ABSTRACT

The present invention relates to aseptic suspensions, physically stable and injectable through a 25G needle or thinner, comprising crystalline, non-micronized 3-beta-hydroxy-5-alpha-pregnan-20-one particles, a mixture of acylglycerols and cholesterol, processes for preparing crystalline, non-micronized, 3-beta-hydroxy-5-alpha-pregnan-20-one suitable for such suspensions, as well as methods for manufacturing such suspensions.

9 Claims, 1 Drawing Sheet

(51) Int. Cl.
 *A61K 47/28* (2006.01)
 *C07J 7/00* (2006.01)
 *A61M 5/32* (2006.01)

(52) U.S. Cl.
 CPC ............ *A61K 9/1688* (2013.01); *A61K 31/57* (2013.01); *A61K 47/14* (2013.01); *A61K 47/28* (2013.01); *C07J 7/002* (2013.01); *A61M 5/32* (2013.01); *C07B 2200/13* (2013.01)

(58) Field of Classification Search
 CPC ...... A61K 47/28; A61M 5/32; C08B 2200/13; B01D 9/0009
 See application file for complete search history.

(56) References Cited

FOREIGN PATENT DOCUMENTS

| WO | 2011087441 | * | 7/2011 |
|---|---|---|---|
| WO | WO2011/087441 A1 | | 7/2011 |

OTHER PUBLICATIONS

Saleki-Gerhardt, A., et al., "Assessment of disorder in crystalline solids," Int. J. Pharmaceutics 1994;101:237-247.
IUPAC Gold Book—Ostwald ripening, downloaded May 24, 2019, https://goldbook.iupac.org/html/O/O04348.html, 1 pg.
International Search Report for PCT Patent App. No. PCT/EP2018/050453 (dated Mar. 20, 2018).
EudraCT No. 2012-004081-18, Sponsor's Protocol Code No. UM104, National Competent Authority: Sweden—MPA, Clinical Trial Type: EEA CTA, Trial Status: Completed, Oct. 23, 2012, Link: https://www.clinicaltrialsregister.eu/ctr-search/trial/2012-004081-18/SE/, 5 pp.

* cited by examiner

INJECTABLE SUSPENSION COMPRISING 3-BETA-HYDROXY-5-ALPHA-PREGNAN-20-ONE, AND A METHOD FOR THE MANUFACTURING THEREOF

CROSS-REFERENCE TO RELATED APPLICATIONS

This application is a National Stage Entry of PCT/EP2018/050453, filed Jan. 9, 2018, which claims priority from Swedish patent application 1750008-3, filed Jan. 9, 2017. The contents of these priority applications are incorporated herein by reference in their entirety.

FIELD OF THE INVENTION

The present invention relates to aseptic suspensions, physically stable and injectable through a 25G needle or thinner, comprising crystalline, 3-beta-hydroxy-5-alpha-pregnan-20-one particles, a mixture of acylglycerols and cholesterol, processes for preparing crystalline non-micronized 3-beta-hydroxy-5-alpha-pregnan-20-one suitable for such suspensions, as well as methods for manufacturing such suspensions.

BACKGROUND OF THE INVENTION 3-beta-hydroxy-5-alpha-pregnan-20-one is a steroid in the pregnane family and a modulator of $GABA_A$-receptor activity indicated for the treatment of a number of CNS disorders, including sex/stress steroid induced conditions (WO99/45931). 3-beta-hydroxy-5-alpha-pregnan-20-one is chemically stable and poorly soluble in most therapeutically acceptable solvents, which makes it difficult to administer the compound to a patient. Further, 3-beta-hydroxy-5-alpha-pregnan-20-one is rapidly metabolized and therefore it is highly desirable to provide an administration with a slower or extended release profile. 3-beta-hydroxy-5-alpha-pregnan-20-one has been administered to monkeys by using a formulation with hydroxypropyl β-cyclodextrin (Grant et al JPET 326:354-362, 2008). Further, formulations comprising 3-beta-hydroxy-5-alpha-pregnan-20-one are disclosed in WO2011/087441. Further, an exploratory clinical study with 3-beta-hydroxy-5-alpha-pregnan-20-one has been published (EudraCT No. 2012-004081-18).

A slower release profile can be obtained by a suspension of a compound in a vehicle in which the compound has some degree of solubility. A drawback and obstacle with such suspensions with crystalline particles for injection is that crystalline particles will grow [(Ostwald ripening, IUPAC, Compendium of Chemical Terminology, 2nd ed. (the "Gold Book") (1997)] and, thereby not physically stable and will be more or less impossible to inject through clinically suitable needles, since such particles will clog in the needle.

It is of outmost importance for a medicinal product for self-administration, to provide a product that is convenient and suitable for the patient without any elaborate special technique. Further, it is necessary that the medicinal product is sterile and stable in order to provide a useful and safe product also after long shelf time.

DESCRIPTION OF THE INVENTION

It is highly desirable, as an objective of the present invention, to provide a suspension comprising a sufficient content, such as at least 10 mg/mL, of 3-beta-hydroxy-5-alpha-pregnan-20-one that is injectable through a 25G needle or thinner, and is stable, wherein said steroid could exert its therapeutic effect in a sufficient manner. Further, it is highly desirable that the suspension remain stable in order to provide a useful suspension also after long shelf time.

Further, it is highly desirable, as an objective of the present invention, to provide a suspension that is sterile and thus suitable for human parenteral use.

The presented technical formulations provided in WO2011/087441, provide the drawback that the methods by which the suspensions are manufactured described therein are not optimized for injection through useful needles (e.g. 25G needles, or thinner) (example 78) or not optimized as a pharmaceutical injection product since the suspension must be stirred for several days (example 77). Stirring for several days is not acceptable according to industry standard and good manufacturing practice as an aseptic process to generate a sterile, parenteral product for human use. Pharmaceutical products for injections shall be sterilized through autoclaving, ionization radiation, or as in the case for the present invention when neither of these are possible, the product components shall be initially sterile and mixed under aseptic conditions (EMA "Guideline on the sterilization of the medicinal product, active substance, excipient and primary container (EMA/CHMP/CVMP/QWP/BWP/850374/2015).

It is thus important that the 3-beta-hydroxy-5-alpha-pregnan-20-one in the medicinal product has the appropriate physical and aseptic properties at time of manufacture and maintain physically stable for adequate time, such as 12 months, or more. Further, the suspension should be injectable through a 25G needle, or thinner.

The present invention surprisingly solves the problem with large multiform lumps when 3-beta-hydroxy-5-alpha-pregnan-20-one is crystallized into particles and the problem of crystal growth with time, by omitting the micronization step when manufacturing such particles and thereby providing a sterile, pharmaceutical, physically stable and injectable suspension, injectable through a 25G needle or thinner, throughout a required shelf-life for a medicinal product, comprising crystalline 3-beta-hydroxy-5-alpha-pregnan-20-one particles, a mixture of acylglycerols and cholesterol.

Before the present invention is described in detail, it is to be understood that the terminology employed herein is used for the purpose of describing particular embodiments only and is not intended to be limiting, since the scope of the present invention will be limited only by the appended claims and equivalents thereof.

It is noted that, as used in this specification and the appended claims, the singular forms "a", "an", and "the" also include plural referents unless the context clearly dictates otherwise.

The term "suspension" is intended to mean dispersion of a solid substance in a continuous phase, which is liquid at room temperature.

The term "pharmaceutical" is intended to mean in the context of the suspensions of the present invention, that the suspensions are in a form that can be used for treatment of intended diseases. This include inter alia that the suspensions must fulfil the medical requirements of safety, and for a product for parenteral use this means the product must be sterile and manufactured under strict aseptic conditions if not possible to terminally sterilize.

The term "injectable" is intended to mean in this context a drug product, i.e. crystalline 3-beta-hydroxy-5-alpha-pregnan-20-one in a suspension that is capable of being dispensed, using a needle and not causing any blockage in the needle and that more or less the entire intended dose can be delivered through the needle.

The term "crystalline" is intended to mean highly ordered arrays of molecules held together by non-covalent interactions. The level or degree of crystallinity is at least 60%, or higher, wherein 100% represents that all material is crystalline. Quantification of crystallinity may be measured by X-ray powder diffraction methods or water vapor sorption measurements as described in Saleki-Gerhardt A et al. Int J Pharm. 1994; 101:237-247.

The term "aseptic" is intended to mean conditions for a process that will result in a sterile product.

The term "sterile" is intended to mean that upon specified tests according to the European pharmacopeia (e.g. Ph. Eur. 2.6.1) and corresponding regional pharmacopeia in other territories (e.g. United States Pharmacopeia, USP) the suspensions of the invention demonstrate no growth of bacteria or fungi or content of bacterial endotoxins.

The term "non-micronized" is intended to mean in this context that the crystalline material has not been exposed to any micronization or nano milling. The grating and sieving steps according to the present invention are not to be viewed as micronization steps.

The term "particles" is intended to mean, in the context of "crystalline, non-micronized 3-beta-hydroxy-5-alpha-pregnan-20-one particles", discrete crystals of 3-beta-hydroxy-5-alpha-pregnan-20-one.

The phrase "grating and sieving" is a delumping procedure intended to break up lumps of aggregated particles (aggregates of crystalline particles of 3-beta-hydroxy-5-alpha-pregnan-20-one). The grating can, for instance, be performed by passing 3-beta-hydroxy-5-alpha-pregnan-20-one particles through a Quadro Comil milling unit fitted with a grating hole screen. The sieving can, for instance (after grating), be performed by passing the grated particles through a Quadro Comil milling unit fitted with a round sieving hole screen.

The term "lumps" is intended to mean, in the context of the present invention, aggregates of crystalline particles of 3-beta-hydroxy-5-alpha-pregnan-20-one, typically held together by weak electrostatic forces.

The term "prefilled syringe" is intended to mean a medical syringe, which can be assembled with a needle or a syringe that is pre-equipped with a needle, which may be delivered to the patient prefilled with one or more doses of the final pharmaceutical composition, such as the suspension of the present invention.

The term "needle" is intended to mean a needle in this context for medicinal administration and includes standard needles of 25G diameter or thinner, such as 26G, 27G, 28G, 29G or 30G diameter. G stands for gauge and is a measure used to define inner and outer diameters of needles. To exemplify this, a regular 25G needle has a nominal inner diameter of about 0.260 mm.

The terms "acylglycerol" and "mixture of acylglycerols" are intended to include all types and combinations of fatty acids esterified to glycerol. A mixture of acylglycerols can for instance consist of various mixtures of monoacylglycerols, diacylglycerols and triacylglycerols. One example of a mixture of acylglycerols is represented by a medium-chain acylglycerol.

An example of a medium chain acylglycerol is medium chain triglyceride (MCT). MCT typically represents a mixture of triglycerides of saturated fatty acids including mainly caprylic acid (octanoic acid, $C_8H_{16}O_2$) and capric acid (decanoic acid, $C_{10}H_{20}O_2$), wherein the total combined percentage of fatty acids with 8 carbon atoms (octanoic acid) and 10 carbon atoms (decanoic acid) is at least 95%. Medium-chain triglycerides may for example be obtained from the oil extracted from the hard, dried fraction of the endosperm of *Cocos nucifera* or from the dried endosperm of *Elaeis guineensis* in a process involving fractionation of the fatty acids, re-estrification and purification.

The mixture of acylglycerols may also be represented by a vegetable oil. Thus, it can be a vegetable oil selected from the group consisting of sesame oil, peanut oil, olive oil, and castor oil, or mixtures thereof.

The mixture of acylglycerols can further comprise a mixture of a vegetable oil and medium-chain acylglycerols.

The suspensions of the invention may comprise additional excipients known to a person skilled in the art such as antioxidants, preservatives, surfactants, coloring, flavoring, or thickening agents.

"Room temperature" denotes a temperature of between 18° C. and 25° C.

By "physically stable" in the context of the present invention intends to mean that the suspension remain injectable after at least 12 months of storage without resuspending the suspension (or minimal resuspension) and with near full or full recovery of dose administered, through a 25G needle, or thinner.

The suspensions of the present invention are preferably administered for pharmaceutical use in therapeutically effective amounts to patients in need thereof. Typically, the suspension is provided by injection parenterally such as subcutaneously, intramuscularly, intracutaneously or intraperitoneally. The therapeutic use is typically for prevention or treatment of conditions of the central nervous system, such as, but not limited to, mood disorders. The formulation of the suspension may be adapted or adjusted according to normal pharmacological procedures, comprising the effective pharmaceutical in a chemical form suitable for the chosen route together with suitable adjuvants, carriers, diluents and vehicles, conventionally used and well-known to a person skilled in the art.

In one aspect of the invention, there is provided a sterile, pharmaceutical, physically stable and injectable suspension, injectable through a 25G needle or thinner, comprising crystalline, 3-beta-hydroxy-5-alpha-pregnan-20-one particles and a mixture of acylglycerols.

In one aspect of the invention, there is provided a sterile, pharmaceutical, physically stable and injectable suspension, injectable through a 25G needle or thinner, comprising the following components:
  sterile, crystalline, 3-beta-hydroxy-5-alpha-pregnan-20-one particles;
  mixture of acylglycerols; and
  cholesterol;
  wherein said suspension is prepared by mixing said components under aseptic conditions within 24 hours or less.

The mixing under aseptic conditions may be carried out for 24, 23, 22, 21, 20, 19, 18, 17, 16, 15, 14, 13, 12 hours, or even for shorter times, such as 6 hours or less.

In one embodiment of this aspect, said suspension is for clinical human parenteral use.

In one embodiment of this aspect, said needle is a 27G needle, or thinner.

In one embodiment of this aspect, the concentration of said 3-beta-hydroxy-5-alpha-pregnan-20-one is 10 mg/mL or higher, such as 11, 12, 13, 14, 15, 16, 17, 18, 19, 20, 21, 22, 23, 24 or 25 mg/mL, or higher.

In one embodiment of this aspect, the concentration of said 3-beta-hydroxy-5-alpha-pregnan-20-one is 25 mg/mL or higher, such as 30, 35, 40, 45, 50, 55, 60, 65, 70 or 75 mg/mL, or higher.

In one embodiment of this aspect, said suspension is injectable without resuspending the suspension and with near full recovery of dose.

The phrase "without resuspending the suspension" includes that the suspension is injectable after minimal resuspension or even without resuspending the suspension and with full or near full recovery of dose.

In one embodiment of this aspect, said crystalline, 3-beta-hydroxy-5-alpha-pregnan-20-one represents non-micronized crystalline, 3-beta-hydroxy-5-alpha-pregnan-20-one.

In one embodiment of this aspect, said crystalline, 3-beta-hydroxy-5-alpha-pregnan-20-one particles remain stable without substantial aggregation during storage.

In one embodiment of this aspect, said suspension remains injectable without careful resuspending the suspension and with full or near full recovery of dose. Preferably, the suspension remains injectable after at least 12 months of storage without resuspending the suspension and with near full recovery of dose. Preferably, the suspension remains injectable after more than 12 months of storage, such as after 18, 24, 30 or 36 months, or more.

In one embodiment of this aspect, said suspension remains injectable after at least 12 months of storage without resuspending the suspension and with full or near full recovery of dose.

In one embodiment of this aspect, the amount of said cholesterol is typically 0.1%-5%, such as 0.1%-2.5%, 0.5%-2%, 0.5%-1.5% or about 1%.

In one embodiment of this aspect, said mixture of acylglycerols is represented by a medium-chain acylglycerol. Preferably, said medium-chain acylglycerol is a medium chain triglyceride (MCT).

In one embodiment of this aspect, said mixture of acylglycerols is represented by sesame oil.

In one embodiment of this aspect, said mixture of acylglycerols represents a mixture of sesame oil and a medium-chain acylglycerol.

In one embodiment of this aspect, there is provided a suspension wherein the components:
  sterile, crystalline, 3-beta-hydroxy-5-alpha-pregnan-20-one particles;
  mixture of acylglycerols; and
  cholesterol;
are mixed under aseptic conditions and prepared within an acceptable time to generate a sterile suspension. Preferably, said components are mixed under aseptic conditions within 24 hours or less, to generate a suspension which is sterile, in accordance with clinical standard, for human parenteral use.

The mixing under aseptic conditions may be carried out for 24, 23, 22, 21, 20, 19, 18, 17, 16, 15, 14, 13, 12 hours, or even for shorter times, such as 6 hours or less.

In one embodiment of this aspect, there is provided a pre-filled syringe equipped with a 27G needle, or thinner, comprising an injectable suspension according to the present invention.

In one aspect of the invention, there is provided an injectable suspension according to the present invention, for clinical human parenteral use.

Suspensions according to the invention may be manufactured as set out below:

Crystalline, 3-beta-hydroxy-5-alpha-pregnan-20-one particles, preferably manufactured as described in the present disclosure, in appropriate amount, is dispensed into a low density polyethylene (LDPE) bag and sealed and the bag is sterilized through gamma irradiation;

The mixture of acylglycerols, preferably MCT, is mixed with cholesterol and stirred until the cholesterol is completely dissolved in the oil;

The MCT/cholesterol mixture is filtered via two 0.22 μm filters and an appropriate amount of this sterile filtered MCT/cholesterol is entered aseptically into a sterile stainless steel compounding vessel in a clean room;

The LDPE bag is adapted to the vessel and the gamma irradiated crystalline, non-micronized 3-beta-hydroxy-5-alpha-pregnan-20-one particles are added aseptically into the vessel. The gamma irradiated crystalline, 3-beta-hydroxy-5-alpha-pregnan-20-one particles are then mixed with MCT/cholesterol with a stirrer for efficient wetting of the powder and efficient mixing; continued for up to 24 hours or less; and under gentle stirring, the suspension is filled aseptically into sterile syringe barrels (prefilled syringes) and thereafter the plungers (stoppers) are introduced.

In one aspect of the invention, there is provided a method of manufacturing a sterile suspension injectable through a 25G needle or thinner, comprising crystalline, non-micronized 3-beta-hydroxy-5-alpha-pregnan-20-one particles; mixture of acylglycerols; and cholesterol; wherein
  crystalline, non-micronized 3-beta-hydroxy-5-alpha-pregnan-20-one particles are sterilized through gamma irradiation;
  the mixture of acylglycerols, preferably MCT, is mixed with cholesterol and stirred until the cholesterol is completely dissolved in the mixture of acylglycerols;
  the mixture of acylglycerols/cholesterol mixture is filtered and entered aseptically into a sterile vessel and said sterilized 3-beta-hydroxy-5-alpha-pregnan-20-one particles is added and mixed for 24 hours, or less; and
  the obtained suspension is filled aseptically into sterile syringe barrels.

The sterilization of said crystalline, non-micronized 3-beta-hydroxy-5-alpha-pregnan-20-one particles may be carried out by dispensing the particles into a low density polyethylene bag and thereafter sterilized through gamma irradiation.

Said sterile vessel may be a sterile stainless steel compounding vessel.

The mixing of the filtered mixture of acylglycerols/cholesterol mixture and said sterilized 3-beta-hydroxy-5-alpha-pregnan-20-one particles is carried out for 24 hours, or less, such as 23, 22, 21, 20, 19, 18, 17, 16, 15, 14, 13, 12 hours, or even for shorter times, such as 6 hours or less.

The crystalline, 3-beta-hydroxy-5-alpha-pregnan-20-one particles, are preferably manufactured by the methods omitting any micronization step as described in the present disclosure.

In one aspect of the invention, there is provided a process of manufacturing crystalline 3-beta-hydroxy-5-alpha-pregnan-20-one particles, comprising:
  (i) dissolving 3-beta-hydroxy-5-alpha-pregnan-20-one in a organic solvent solution with a water content of at least 0.1% (v/v), at a temperature of at least 45° C.;

(ii) adding the solution of step (i) into liquid alkane holding a temperature of 10° C. or lower, and stirring said solution mixture to obtain precipitation of crystalline 3-beta-hydroxy-5-alpha-pregnan-20-one; followed by;

(iii) filtering and drying the precipitated crystalline 3-beta-hydroxy-5-alpha-pregnan-20-one obtained in step (ii);

wherein any micronization step of said crystalline 3-beta-hydroxy-5-alpha-pregnan-20-one particles is omitted.

In one embodiment of this aspect, said organic solvent solution is a tetrahydrofuran solution.

In one embodiment of this aspect, said method comprises the additional step of grating and sieving the crystalline 3-beta-hydroxy-5-alpha-pregnan-20-one particles obtained in step (iii). This may be carried out in order to minimize formation of lumps of said particles.

In one embodiment of this aspect, said tetrahydrofuran solution has water content of from 0.5% to 1.5% (v/v).

In one embodiment of this aspect, said tetrahydrofuran solution with water content holds a temperature of about 50° C.

In one embodiment of this aspect, said liquid alkane holds a temperature of from −10° C. to −20° C.

In one embodiment of this aspect, said liquid alkane is liquid heptane.

In one embodiment of this aspect, there is provided crystalline 3-beta-hydroxy-5-alpha-pregnan-20-one particles, obtainable by a process according to this aspect.

In one aspect of the invention, there is provided a sterile, pharmaceutical, physically stable and injectable suspension, injectable through a 25G needle or thinner, comprising the following components:
sterile, crystalline, non-micronized 3-beta-hydroxy-5-alpha-pregnan-20-one particles;
mixture of acylglycerols; and
cholesterol;
wherein said suspension is prepared by mixing said components under aseptic conditions within 24 hours or less; and
wherein said crystalline, 3-beta-hydroxy-5-alpha-pregnan-20-one particles are manufactured according to the process aspect as set out above.

In one aspect of the invention, there is provided a pre-filled syringe equipped with a 27G needle, comprising a suspension according to the present invention, said suspension comprising crystalline 3-beta-hydroxy-5-alpha-pregnan-20-one particles obtainable by the process according to the present invention.

In one aspect of the invention, there is provided a suspension according to the present invention, for use in therapy.

The invention will now be described by a number of illustrative, non-limiting examples.

EXAMPLE 1

Testing Injectability and Stability of Suspensions, Comprising Crystalline, Non-Micronized, 3-beta-hydroxy-5-alpha-pregnan-20-one According to the Present Invention Injectability and stability of suspensions with a composition according to example 6 produced by stirring at large scale (1.9 L MCT) and including crystalline 3-beta-hydroxy-5-alpha-pregnan-20-one one was made as described in example 8 was evaluated by passing the suspension through syringes equipped with G25, G27 or G30 needles. Each time an obstruction was observed, the needle was exchanged for a new needle, and the number of obstructions per total gram (s/g) of evaluated suspension was recorded. Normally manual pressure was used to expel the suspension. Syringes: Luer-Lock Plastic Syringes, 3 mL (National Scientific Company. Rockwood, Tenn., USA). The suspension was first aspirated directly into the syringe or using an 18G×2" needle, (Terumo, Belgium). Needles tested were G25×5/8, G27×1/2 and G30×1/2 (Henke Sass Wolf, Tuttlingen, Germany). Injectability after manufacture is shown in Table 1 below. Injectability after 12 months storage under varying storage conditions is depicted in Table 2 below.

TABLE 1

Injectability of a suspension at 40 mg/mL strength
Number of stops/gram suspension (s/g) for different needles. Total amount of suspension tested was 3 g for each condition.

| G25 s/g | G27 s/g | G30 s/g |
|---|---|---|
| 0 | 0 | 0.3 |

Good injectability was also obtained with a similar suspension made in smaller scale (according to example 7 after grating and sieving) showing zero (0) stops in a G27 needle with 2.8 g suspension.

TABLE 2

Injectability after 12 months storage of the 40 mg/mL suspension under different conditions. Number of stops/gram suspension (s/g) for different needles. Amount of suspension tested was 3 g for each condition.

| Condition | G25 s/g | G27 s/g | G30 s/g |
|---|---|---|---|
| ambient | 0 | 0 | 1.9 |
| refrigerated | 0 | 0 | 1.0 |
| cycled | 0 | 0 | 0.7 |

Ambient condition represents non-controlled room temperature. In cycled condition the temperature was cycled from refrigerated (about +2° C.) to ambient (about +20° C.) once per 24 hours. Refrigerated condition is +2 to +8° C.

The results in Tables 1 and 2 provide that the suspensions of the invention, comprising crystalline, non-micronized 3-beta-hydroxy-5-alpha-pregnan-20-one are stable and injectable in at least a G27 needle also after 12 months of storage and under varying storage conditions.

EXAMPLE 2

Comparative Testing of Injectability of Suspensions, Comprising Crystalline, Non-Micronized, 3-beta-hydroxy-5-alpha-pregnan-20-one (A) with Comparative Suspensions as Described in WO2011/087441, Comprising Micronized, Crystalline 3-beta-hydroxy-5-alpha-pregnan-20-one (B)

Injectability of a suspension according to the invention (A) was compared with injectability of a suspension with the same compounding method and composition (40 mg/mL irradiated 3-beta-hydroxy-5-alpha-pregnan-20-one in sterile filtered MCT with 1% added and dissolved cholesterol, produced aseptically at 1.9 L scale), where the crystalline 3-beta-hydroxy-5-alpha-pregnan-20-one, however, had been micronized to reach a corresponding primary particle size as in A prior to suspension preparation (B). The suspension B represents a suspension as presented in example 78 of WO2011/087441. A similar suspension was used in an explorative clinical study (EudraCT No. 2012-004081-18), however, a larger diameter needle was used to avoid blockage of the injection needle.

The suspension according to the invention (A) was based on 3-beta-hydroxy-5-alpha-pregnan-20-one, made with a similar method as the one described in example 7 but without the subsequent delumping (grating and sieving) step. The crystalline material had a mean particle size in a volume distribution (D50) of the powder of about 8 μm. This was determined by Light Diffraction in an aqueous system on a Malvern Mastersizer 3000 using conventional procedures. A Fraunhofer calculation model was used for evaluation.

For the comparative suspension preparations (B), 3-beta-hydroxy-5-alpha-pregnan-20-one conventionally crystallized (prepared as set out in Example 9) and thus in the form of a white powder with large flake-like crystals up to 0.5×0.5 mm size was micronized under nitrogen gas using fluid energy jet mills by Micron Technologies Ltd. (Dartford, UK). The mean particle size in a volume distribution (D50) of the micronized powder was 7-8 μm determined as described above.

The injectability of the comparative suspension B was tested as described in example 1 and provided 1 stop/gram tested suspension in 25G and 12 stops per gram tested in 27G needles (see Table 3). According to Table 3 below, the injectability for suspension A made from non-micronized 3-beta-hydroxy-5-alpha-pregnan-20-one as described above was dramatically improved, even without the crystalline material being further optimized by grating and sieving.

TABLE 3

Injectability of a 40 mg/mL suspension of non-micronized 3-beta-hydroxy-5-alpha-pregnan-20-one (A) compared to a corresponding suspension of micronized 3-beta-hydroxy-5-alpha-pregnan-20-one (B). Number of injection stops/gram suspension (s/g) for different needles. Amount of suspension tested was 2-3 g for each condition except only 0.9 g for B in G27.

|  | G25 s/g | G27 s/g |
|---|---|---|
| A: non-micronized suspension according to the invention with 3-beta-hydroxy-5-alpha-pregnan-20-one | 0 | 0.8 |
| B: comparative micronized suspension with 3-beta-hydroxy-5-alpha-pregnan-20-one | 1 | 12 |

The results show that micronized crystalline 3-beta-hydroxy-5-alpha-pregnan-20-one, as described in WO2011/087441, despite having a small particle size, provides a suspension that is not operational for injection, whereas with applying the methods in manufacturing crystalline, 3-beta-hydroxy-5-alpha-pregnan-20-one with optimized particle properties, without introducing micronization, and which may be further grated and sieved, surprisingly provides a suspension where the injectability is significantly improved and operational.

EXAMPLE 3

Stability and Injectability of a Suspension Comprising Crystalline, Non-Micronized, 3-beta-hydroxy-5-alpha-pregnan-20-one at 40 mg/mL in Pre-Filled Syringes A suspension according to example 6 produced by stirring at a larger scale (1.9 L MCT) including crystalline 3-beta-hydroxy-5-alpha-pregnan-20-one one was made with a similar method as the one described in example 8 was filled in syringes equipped with 27G needles and stoppered by stoppers (Hypack SCF Becton & Dickinson and Company). Filling weight was 0.5 g with the suspension having a density of about 0.95 g/mL.

The syringes were stored horizontally at 5° C., 25° C./60% RH and 40° C./75% RH, respectively, for up to twelve months. The total amount of active substance recovered when the syringe was emptied through the 27G needle was measured by gas chromatography as mg active compound per syringe on 5 syringes at each pull date and storage condition. The syringes were taken directly from storage and not resuspended, mixed or shaken before ejection and assaying. Results are provided in Table 4. Similar results were obtained when syringes were stored vertically, at similar conditions with similar content.

TABLE 4

Recovered dose from syringes pre-filled (mean of 10) with suspension of 3-beta-hydroxy-5-alpha-pregnan-20-one according to example 1, and stored up to 27 months, equipped with a 27 G needle in different conditions. Suspensions were not resuspended before ejection. Recovered dose*
Filling weight 0.5 g suspension (40 mg/mL), density 0.95 g/mL

| Initial | 21.1 (20.4-21.7) mg | 97.5% |
|---|---|---|
|  | 5° C. |  |
| 3 months | 21.5 (21.2-21.6) mg | 98.9% |
| 6 months | 22.3 (21.3-22.9) mg | 99.5% |
| 12 months | 22.1 (21.7-22.9) mg | 100.7% |
|  | 25° C./65% RH |  |
| 3 months | 21.7 (21.3-22.2) mg | 99.9% |
| 6 months | 21.6 (21.2-22.1) mg | 99.7% |
| 12 months | 21.2 (20.7-21.8) mg | 100.0% |
| 36 months | 21.8 (21.4-22.3) mg | 103.8% |
|  | 40° C./75% RH |  |
| 3 months | 21.5 (21.3-22.0) mg | 100.1% |
| 6 months | 21.0 (20.6-21.6) mg | 99.1% |
| 12 months | 21.6 (21.3-21.9) mg | 103.6% |

*Recovered dose in mg and expressed as percentage of filled amount

Thus the intended dose could be ejected with good precision even after 12 months storage (at 5° C., 25° C. and 40° C.) and after 36 months stored in 25° C. of the suspension in a syringe through a 27G needle without any effort to resuspend the suspension before use. Thus, surprisingly no apparent particle size change (or other change) which could affect injectability appeared in the suspension, even after 12 months storage. Syringes which were fully resuspended also gave similar recovery results. Primary particle size of the crystalline 3-beta-hydroxy-5-alpha-pregnan-20-one remained unchanged during storage.

EXAMPLE 4

Testing of Injectability of Suspensions, Comprising Crystalline, Non-Micronized, 3-beta-hydroxy-5-alpha-pregnan-20-one at Different Strengths Suspensions were prepared at a concentration of 10, 25, 40, 75, 150, 200 and 300 mg/mL, respectively, of 3-beta-hydroxy-5-alpha-pregnan-20-one in MCT. 3-beta-hydroxy-5-alpha-pregnan-20-one (as prepared as set out in example 8) was weighed into 15 mL vials provided with a magnetic stir bar and MCT oil with 1% added and dissolved cholesterol, was added. The suspensions were stirred for one hour at 1000 rpm. All suspensions were fluid but the 300 mg/mL suspension was very viscous. Injectability of the suspensions was tested in 27G needles for the 10, 75 and 200 mg/mL suspensions and zero (0) stops appeared for any of the suspensions when 2.6 to 3 g suspension was tested.

EXAMPLE 5

Testing of Injectability of Suspensions Comprising Crystalline, Non-Micronized, 3-beta-hydroxy-5-alpha-pregnan-20-one in an Oily Phase of Sesame Oil or MCT or Mixtures thereof, with or without 1% Added Cholesterol in a Pre-Filled Syringe To five 60 mL glass tubes were weighed 500+/−1 mg 3-beta-hydroxy-5-alpha-pregnan-20-one prepared as described in example 8. To the tubes was added sesame oil with or without 1% added and dissolved cholesterol, or MCT with or without 1% added and dissolved cholesterol or a mixture of 20% (w/w) sesame oil and 80% (w/w) MCT, with 1% added and dissolved cholesterol. All tubes were shaken briefly to make course suspensions just after addition of oil. Subsequently they were rotated over the top at 50 rpm for 23 hours to produce fine suspensions. The suspensions were filled (about 0.4 mL) in pre-filled syringes equipped with 27G needles and stoppered by stoppers (Hypack SCF Becton & Dickinson and Company). After 7 weeks ambient storage (non-controlled room temperature) standing with needle down, all the suspensions in one syringe for each suspension could easily be expelled completely without stops or any obstruction in the needle.

EXAMPLE 6

Process for Preparing Injectable Suspensions, Comprising Crystalline, Non-Micronized 3-beta-hydroxy-5-alpha-pregnan-20-one 2446.1 mg crystalline, non-micronized 3-beta-hydroxy-5-alpha-pregnan-20-one prepared according to example 8 was suspended in 58.09 g MCT (Captex 355 EP/NF, ABITEC corp, Janesville, Wis., USA) including 1% (w/w) added and dissolved cholesterol (providing a 3-beta-hydroxy-5-alpha-pregnan-20-one concentration of about 40 mg/mL) in a 100 mL flask with a straight, long magnetic stir bar and stirred at 800 rpm giving a pronounced vortex. After 30 minutes, the suspension was visibly homogenous. After 3 hours there were no visible particles on the bottom of the flask and the mean particle size (D50) was about 7.6 µm.

Similar results (D50=7.7 µm) were obtained when the process for making suspension was further scaled up to 1.9 L production scale.

The particle size distributions were determined by light diffraction using conventional methods on a Malvern Mastersizer 3000. Samples of suspensions were added to circulating silicon oil. A Fraunhofer calculation model was used for evaluation. D50 represents the particle size (µm) in the respective percentiles of the volume size distribution, as described in ISO Guideline 13320-1.

EXAMPLE 7

Process for Manufacturing Crystalline, Non-Micronized, 3-beta-hydroxy-5-alpha-pregnan-20-one with Optimized Particle Properties that is Grated and Sieved 3-beta-hydroxy-5-alpha-pregnan-20-one (307 g) in THF solution (5.2 L, 17 mL/g of 3-beta-hydroxy-5-alpha-pregnan-20-one) was added to a nominal 5 L reactor, the jacket temperature was set to 50° C., and the mixture was stirred until a clear solution was obtained. Tap water (48 g) was then added to the solution. Thus the water content in THF was 0.9% (v/v).

Heptane (15.4 L) was charged to a 50 L reactor with controlled jacket temperature under rapid stirring. When the internal temperature of the heptane had reached −14° C., the hot THF solution of 3-beta-hydroxy-5-alpha-pregnan-20-one was added over the course of 5 minutes, causing rapid crystallization of 3-beta-hydroxy-5-alpha-pregnan-20-one. After completed addition, the temperature of the resulting slurry was −8° C.

The jacket temperature of the 50 L reactor was thereafter set to 5° C., and the slurry was stirred for 1 hour 48 minutes. The slurry (temperature 5° C.) was filtered on a 25 µm mesh size nylon filter cloth. Filtration time: 15 minutes. The filter cake was washed with two 5 L portions of heptane (ambient temperature). The product was first dried by sucking air through the filter cake for 5 hours at room temperature. After one hour, the material was divided finely using a metal spoon. After air-drying, the material was further dried in a vacuum oven overnight (40° C., vacuum with a small air-bleed, 14 h). Yield: 249.0 g (81%).

In subsequent steps, this material (crystalline, non-micronized 3-beta-hydroxy-5-alpha-pregnan-20-one) was further grated and sieved (de-lumped) in two steps:

Grating Step

Material obtained above (226.5 g) was grated by passing it through a Quadro Comil milling unit fitted with a 1.0 mm grating hole screen and a square impeller. The impeller speed was mainly set at 1000-1600 rpm, and periodically raised briefly to 4500 rpm to clear the screen. The material was passed through the screen in 40 minutes. Yield: 191.3 g (84%).

Sieving Step

Material from the grating step above (171.1 g) was sieved by passing through a Quadro Comil milling unit fitted with a 610 µm round hole screen and a round impeller. The impeller speed was mainly set at 1000-1400 rpm. The material was passed through the screen in 25 minutes. Yield: 132.9 g (78%). The effect of the delumping process was verified by filtration of suspension samples on 500 µm stainless steel screen filters (Test sieve, S/N 02007758, Retsch, Germany).

Figure 1A:
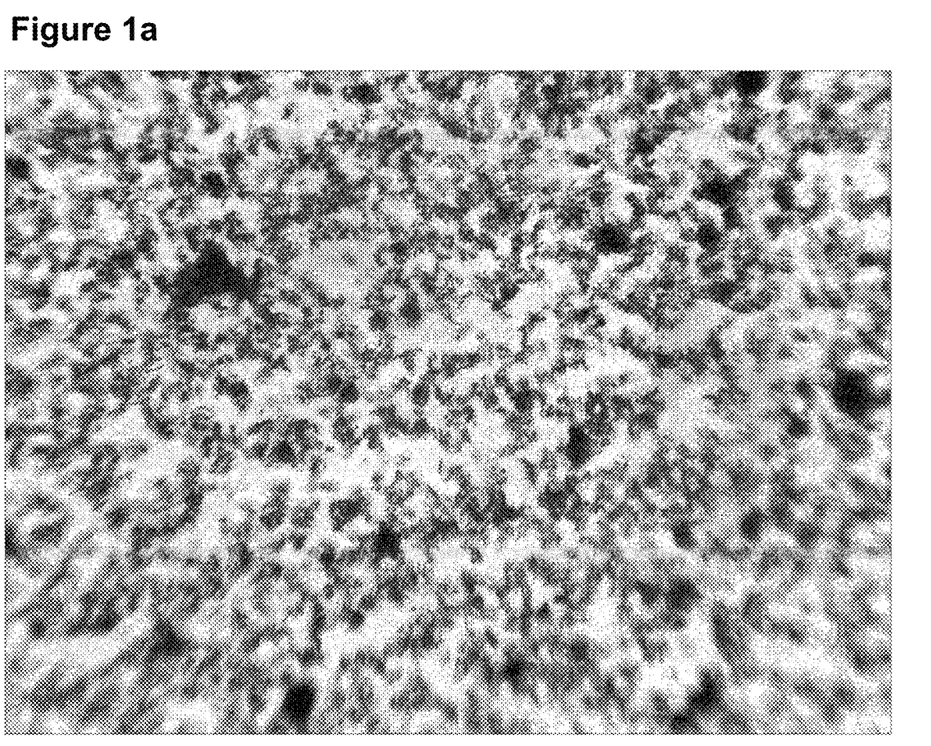
FIG. 1a provides a light microscopy photo of crystalline particles in a suspension of the present invention including 3-beta-hydroxy-5-alpha-pregnan-20-one wherein said particles have been grated and sieved (delumped).
Figure 1B:
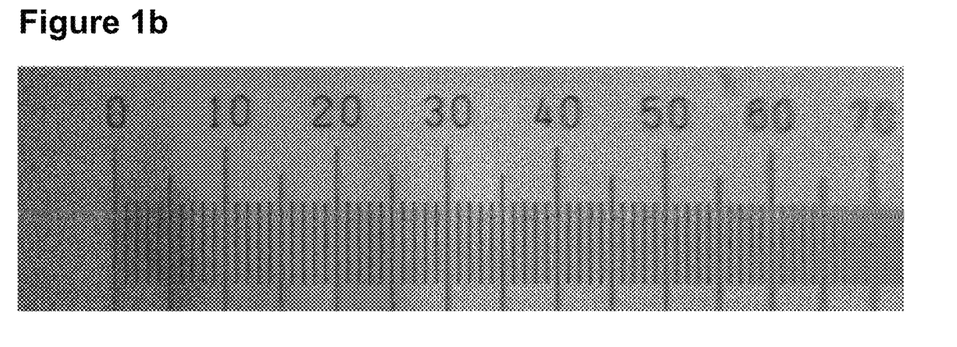
FIG. 1b provides size scale, where one division is 10 μm. Both photos (1a and 1b) are taken at the same magnification. Further details are set out in Example 7.

Test suspensions for verification of grating and sieving (delumping) efficacy were prepared as follows: To 160 mg of 3-beta-hydroxy-5-alpha-pregnan-20-one before the grating step and after the sieving step, respectively, was added 3.8 g of MCT in a 16 mL test tube. These suspensions were rotated over the top at 50 rpm, for 24 hours. Filtration of the resulting suspensions on a 0.5 mm stainless steel filter screen demonstrated some residual lumps on the screen for the suspension sample before the grating step but no lumps for the sample after the sieving step. FIG. 1a provides a light microscopy photo of crystalline particles in test suspension of the present invention. FIG. 1b provides size scale, where one division is 10 µm. Both photos (1a and 1b) are taken at the same magnification.

EXAMPLE 8

Large Scale Process for Manufacturing Crystalline, Non-Micronized, 3-beta-hydroxy-5-alpha-pregnan-20-one with Optimized Particle Properties that are Further Grated and Sieved 3-beta-hydroxy-5-alpha-pregnan-20-one (7.55 kg) and THF (132 L) was charged into a 800 L-reactor under inert atmosphere. The mixture was warmed to 65° C. and stirred until a clear solution was obtained. Purified water (1.07 kg, 0.8% (v/v) water in THF) was added and the obtained solution was transferred to a new, clean barrel (the barrel had been kept warm with warm tap water, approx. 45° C.). The reactor was then cleaned and n-heptane (400 L) was charged to the reactor. When Ti in the reactor reached −12° C., the THF solution from the barrel was charged to the reactor (charging took 17 minutes). The obtained slurry was filtered, washed with n-heptane (20 L) and air-dried for 48 hours. Yield: 6.8 kg (90%). The material was further grated and sieved ("de-lumped") by passing it through a Quadro Comil milling unit fitted with a 1.0 mm grating hole screen and a square impeller, followed by passing (sieving) through a Quadro Comil milling unit fitted with a 610 µm round hole screen and a round impeller to give 5.5 kg final product.

EXAMPLE 9

Large Scale Process for Manufacturing Crystalline, Micronized, 3-beta-hydroxy-5-alpha-pregnan-20-one with Purification Crude 3-beta-hydroxy-5-alpha-pregnan-20-one (14.8 kg) and THF (72 L) was charged into a 800 L-reactor under inert atmosphere. The mixture was warmed to 65° C. and n-heptane (120 L) was charged to the mixture keeping Ti=60-70° C. The mixture was stirred for 30 minutes at this temperature, after which Tj was set to 20° C. and the mixture was stirred for 3 hours. The slurry was filtered and the substance was air-dried for approximately 6 hours. The product was recrystallized in the same manner two more times, using 65 L of THF and 110 L of n-heptane in the second recrystallization, and 60 L of THF and 100 L of n-heptane in the third. After the last recrystallization the product was washed on the filter with 30 L of n-heptane before air-drying. Yield: 7.56 kg (51%). The product was micronized under nitrogen gas using fluid energy jet mills by Micron Technologies Ltd. (Dartford, UK), until a desired size of the particle (a particle size in a volume distribution (D50) of the powder of about 7-8 µm) was obtained. Material produced as set out in this example was used for comparative testing, e.g. for the comparative suspension preparations (B), as described in Example 2.

EXAMPLE 10

Comparative Testing of Injectability of Suspensions, Comprising Crystalline, Non-Micronized, 3-beta-hydroxy-5-alpha-pregnan-20-one According to the Invention (C) with a Comparative Suspension as Described in WO2011/087441 (D)

Suspension C and D were both produced in small scale using the same compounding method and composition (10 mg/mL 3-beta-hydroxy-5-alpha-pregnan-20-one in sesame oil with 1% added and dissolved cholesterol, produced at 20 mL scale), on a magnetic stirrer at about 500 rpm using a conventional Teflon coated stir bar, at room temperature for several days. Injectability of the suspensions C and D was determined after 19 hours stir, after 6 days stir and after 9 days stir, as described in Example 1. The suspension D represents a suspension as presented in example 77, of WO2011/087441.

The suspension according to the invention (C) was based on 3-beta-hydroxy-5-alpha-pregnan-20-one, prepared as described in Example 8.

For the comparative suspension preparation (D), 3-beta-hydroxy-5-alpha-pregnan-20-one conventionally crystallized (e.g. according to Example 9) in the form of a white powder with large flake-like crystals up to 0.5×0.5 mm size was used.

The injectability of the comparative suspension D was tested as described in Example 1 and provided 48 stops per gram tested suspension in 25G needles after 19 hours stir and 3.8 stops per gram tested in 27G needles after 6 days of stir (see Table 4). According to Table 4 below, the injectability for suspension C made from crystalline, non-micronized, 3-beta-hydroxy-5-alpha-pregnan-20-one made according to the present invention as described above was dramatically better after 19 hours stir, with no stop in a G27 needle, as compared to the results for suspension D even after 6 days of stir when the estimated primary particle size of 3-beta-hydroxy-5-alpha-pregnan-20-one in suspension D is similar to that of suspension C stirred for 19 hours. After 9 days stir, both suspensions had no stops in G27 needles.

TABLE 4

Injectability of a 10 mg/mL suspension of non-micronized 3-beta-hydroxy-5-alpha-pregnan-20-one (C) compared to a corresponding suspension of conventionally crystallized 3-beta-hydroxy-5-alpha-pregnan-20-one (D).
Number of injection stops per gram suspension (s/g). Amount of suspension tested was 3 g for each condition except only 0.3 g for D with 19 h stir.

|  | 19 hours stir | | 6 days stir | |
| --- | --- | --- | --- | --- |
|  | s/g | Needle | s/g | Needle |
| C: non-micronized suspension according to the invention with 3-beta-hydroxy-5-alpha-pregnan-20-one | 0 | G27 | 0 | G27 |
| D: comparative suspension with conventionally crystallized 3-beta-hydroxy-5-alpha-pregnan-20-one | 48 | G25 | 3.8 | G27 |

The results show that preparation of a suspension of conventionally crystallized 3-beta-hydroxy-5-alpha-pregnan-20-one, as described in WO2011/087441 example 77, provides a suspension that is not operational for injection, when the production (stir) time is within acceptable limits (19 hours). For a suspension as described in WO2011/087441, a production time of several days is necessary to produce a suspension where the injectability is just about acceptable. Such prolonged production time is deemed unacceptable according to current Good Manufacturing Practice, taking into account the absolute demand of sterility for a pharmaceutical suspension for parenteral use. Using crystalline, 3-beta-hydroxy-5-alpha-pregnan-20-one with optimized properties, according to the invention, surprisingly provides a suspension where the injectability is significantly improved and operational with an acceptable process time for a pharmaceutical suspension for parenteral use.

The invention claimed is:
1. A process of manufacturing non-micronized crystalline 3-beta-hydroxy-5-alpha-pregnan-20-one particles, comprising:

(i) dissolving 3-beta-hydroxy-5-alpha-pregnan-20-one in an organic solvent solution with a water content of at least 0.1% (v/v), at a temperature of at least 45° C.;

(ii) adding the solution of step (i) into liquid alkane at a temperature of 10° C. or lower, and stirring said solution mixture to obtain precipitation of crystalline 3-beta-hydroxy-5-alpha-pregnan-20-one; followed by (iii) filtering and drying the precipitated crystalline 3-beta-hydroxy-5-alpha-pregnan-20-one obtained in step (ii); wherein any micronization step of said crystalline 3-beta-hydroxy-5-alpha-pregnan-20-one particles is omitted.

2. The process according to claim 1, wherein said organic solvent solution is a tetrahydrofuran solution.

3. The process according to claim 1, comprising the additional step of grating and sieving the crystalline 3-beta-hydroxy-5-alpha-pregnan-20-one particles obtained in step (iii).

4. The process according to claim 1, wherein said tetrahydrofuran solution has water content of from 0.5% to 1.5% (v/v).

5. The process according to claim 4, wherein said tetrahydrofuran solution with water content is held at a temperature of about 50° C.

6. The process according to claim 1, wherein said liquid alkane is held at a temperature of from −10° C. to −20° C.

7. The process according to claim 1, wherein said liquid alkane is liquid heptane.

8. A method of manufacturing a sterile suspension injectable through a 25G needle or thinner, comprising crystalline, non-micronized 3-beta-hydroxy-5-alpha-pregnan-20-one particles; mixture of acylglycerols; and cholesterol; comprising the steps of sterilizing crystalline, non-micronized 3-beta-hydroxy-5-alpha-pregnan-20-one particles with gamma irradiation;

mixing the mixture of acylglycerols with cholesterol and stirring until the cholesterol is completely dissolved in the mixture of acylglycerols;

filtering the mixture of acylglycerols/cholesterol mixture aseptically into a sterile vessel, adding said sterilized 3-beta-hydroxy-5-alpha-pregnan-20-one particles and mixing for 24 hours, or less; and filling sterile syringe barrels with the obtained suspension.

9. The method according to claim 8, wherein said crystalline, 3-beta-hydroxy-5-alpha-pregnan-20-one particles are manufactured by a process comprising the steps of:

i) dissolving 3-beta-hydroxy-5-alpha-pregnan-20-one in an organic solvent solution with a water content of at least 0.1% (v/v), at a temperature of at least 45° C.;

(ii) adding the solution of step (i) into liquid alkane at a temperature of 10° C. or lower, and stirring said solution mixture to obtain precipitation of crystalline 3-beta-hydroxy-5-alpha-pregnan-20-one; followed by;

(iii) filtering and drying the precipitated crystalline 3-beta-hydroxy-5-alpha-pregnan-20-one obtained in step (ii); wherein any micronization step of said crystalline 3-beta-hydroxy-5-alpha-pregnan-20-one particles is omitted.

* * * * *